United States Patent [19]
Evans et al.

[11] Patent Number: 5,358,532
[45] Date of Patent: Oct. 25, 1994

[54] CEMENTLESS ACETABULAR CUP

[75] Inventors: David L. Evans, Bartlett; Peter E. Stegemann; Robert-Jan Enzerink, both of Memphis, all of Tenn.

[73] Assignee: Smith & Nephew Richards Inc., Memphis, Tenn.

[21] Appl. No.: 900,059

[22] Filed: Jun. 16, 1992

[51] Int. Cl.$^5$ ............................................. A61F 2/34
[52] U.S. Cl. ...................................................... 623/22
[58] Field of Search ........................ 623/22, 18, 23, 12

[56] References Cited

U.S. PATENT DOCUMENTS

| | | | |
|---|---|---|---|
| 3,820,167 | 6/1974 | Sivash | 623/22 |
| 3,840,904 | 10/1974 | Tronzo | 623/22 |
| 3,859,669 | 1/1975 | Shersher | 623/22 |
| 4,695,282 | 9/1987 | Forte et al. | 623/22 |
| 4,704,127 | 11/1987 | Averill et al. | 623/22 |
| 4,813,959 | 3/1989 | Cremascoli | 623/22 |
| 4,834,759 | 5/1989 | Sportono et al. | 623/22 |
| 4,892,549 | 1/1990 | Figgie, III et al. | 623/22 |

FOREIGN PATENT DOCUMENTS

| | | | |
|---|---|---|---|
| 0291562 | 11/1988 | European Pat. Off. | 623/22 |
| 0346270 | 12/1989 | European Pat. Off. | 623/22 |
| 3602081 | 10/1986 | Fed. Rep. of Germany | 623/22 |
| 2548012 | 1/1985 | France | 623/22 |
| 2626168 | 7/1989 | France | 623/22 |
| 2653326 | 4/1991 | France | 623/22 |

Primary Examiner—David Isabella
Attorney, Agent, or Firm—Pravel, Hewitt, Kimball & Krieger

[57] ABSTRACT

A prosthetic joint acetabular cup component is provided that can be press fit into a patient's acetabulum, to create an interference fit and to eliminate the need for cement. A body portion of the cup provides an outer convex surface, The inside of the cup provides an inner concave surface. An apex portion of the cup or shell is spaced from the lower rim portion, the lower rim defining a plane. A plurality of annular rings are spaced along the body outer surface beginning at the lower rim and extending at least a partial distance toward the apex. Each of the annular rings is preferably generally parallel to the plane of the lower rim.

12 Claims, 4 Drawing Sheets

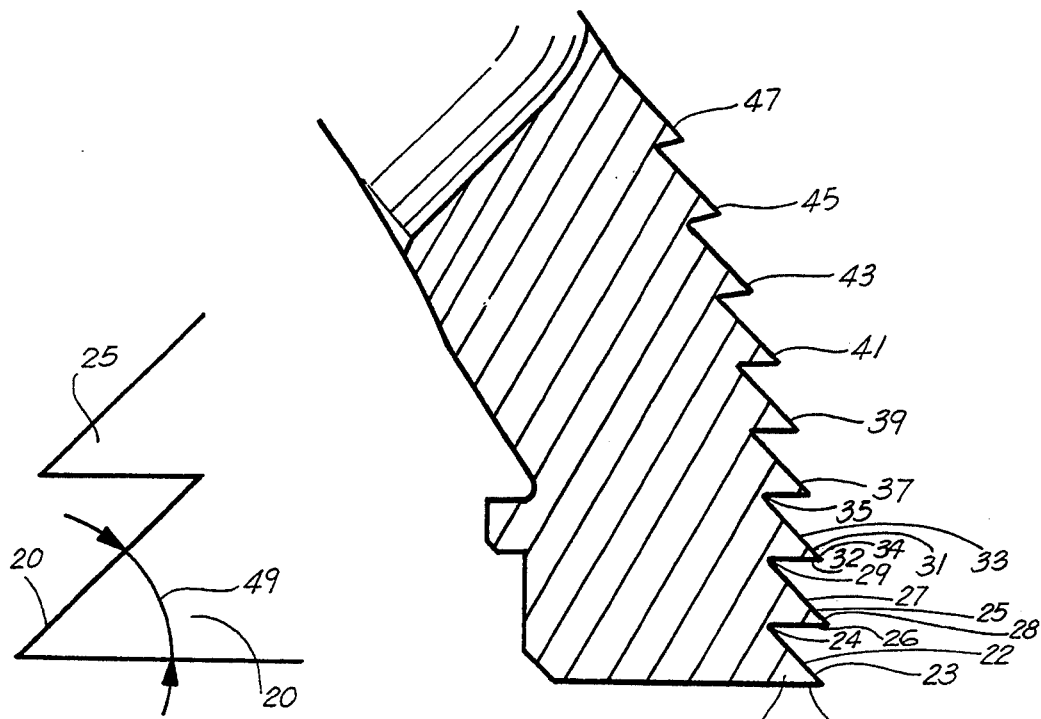
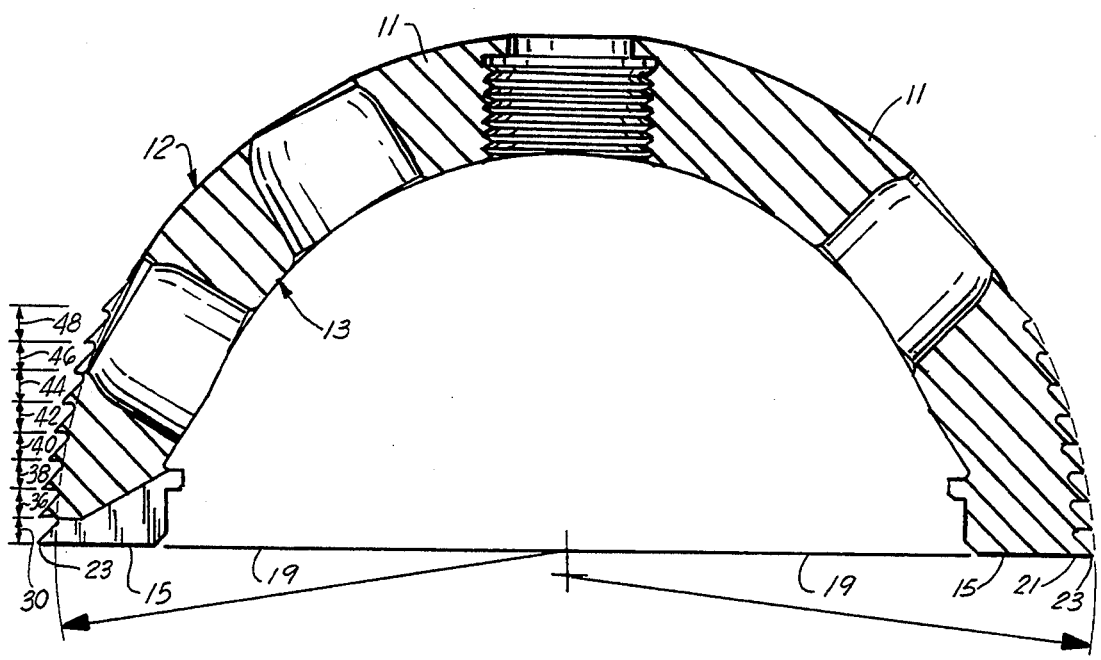

CEMENTLESS ACETABULAR CUP

BACKGROUND OF THE INVENTION

1. Field Of The Invention:

The present invention relates to medical prosthetic implant devices and more particularly to an acetabular cup component to be fitted to a patient's acetabulum. Even more particularly, the present invention relates to a cementless acetabular cup component to be used in total hip replacement wherein there is provided an improved outer surface geometry that affixes the cup to the acetabulum with a plurality of annular, spaced apart rings, allowing a cementless press fit of the cup to the acetabulum.

2. General Background:

Total hip replacement has become a standard operation in orthopaedics for the relief of pain and restoration of function in patients who are incapacitated from disease or injury. Early total hip replacement implants were affixed to bone by means of bone cement. With time and experience, it was learned that bone cement has a finite lifetime and may fail by cracking, especially if in service for many years.

Cement failure leads to implant loosening, pain and loss of function, requiring operative intervention for correction. In the early 1980's, cementless fixation of total hip replacement implants was proposed as an alternative to cemented total hip replacement implants, on the basis that elimination of the weak link in fixation would increase the service life of total hip replacement implants.

Prior art approaches to cementless acetabular replacement include threaded components which are affixed to the acetabulum by means of screw threads. Threaded components were originally conical in shape; however, because of difficulty in placement, more recent designs have a more spherical shape. The threads of these cups are sufficiently deep to require screwing the cup into a prepared cavity for insertion. The primary disadvantage of threaded cups is the difficulty of insertion, which can lead to technical errors and poor results.

Another approach to this problem has been the spherical cup with a porous metal coating on the fixation surfaces. These cups have been affixed with a variety of fasteners, including screws, spikes and interference fits.

Screw and spike fixation have been shown to be effective; however, there are inherent risks associated with these fasteners. Surgical errors in the placement of screws have led to injuries of vital blood vessels proximate to the acetabulum, sometimes leading to the deaths of patients.

A longer term risk associated with these fixation means is the potential for fretting between the spikes/screws and the metal cup. Fretting will generate particulate metal debris which may lead to irritation and loosening of the cup, or malignant tissue responsive in the patient.

Interference fits of spherical cups are achieved by preparing the acetabulum with a diameter slightly smaller than the outer diameter of the cup which will be used. The cup is then impacted into the acetabulum during which the cavity expands to receive the cup. The expansion is partly elastic and results in a residual hoop stress in the bone at the cup/bone interface. The hoop stress applies pressure to the cup which is sufficiently large to retain it in position.

The primary disadvantage associated with spherical cups that are fit by interference is that there is very little mechanical interlock between the cup and bone. The small amount of mechanical interlock in many cases may not be sufficient to resist forces transmitted through the cup, especially if the quality of the surrounding bone is poor. Insufficient interlock would likely lead to loosening of the cup and require surgical intervention to correct.

One design which relies on this spherical cup interference fit fixation method is that which is described in U.S. Pat. No. 4,892,549 entitled "Dual Radius Acetabular Cup Component" issued to Figgie et. al. and assigned to Osteonics Corporation. The '549 patent describes a dual radius acetabular cup component which is currently marketed by Osteonics Corporation. The dual radius cup relies on an interference fit of the larger spherical surface adjacent to the rim of the cup. The Osteonics design seeks to improve the interference fit by limiting it to the portion of the cup adjacent to the rim. This should provide increased pressure during insertion compared to a cup with one continuous spherical radius. The increased pressure should provide an improved interference fit.

There are two disadvantages to the Osteonics design. First, the design has a rim at an intermediate position on the surface of the cup (transition from the first to the second spherical radius) which provides resistance to insertion. In an acetabulum which has been reamed to the size of the smaller radius, the rim will scrape bone away from the fixation surface during insertion. The removal of bone will lessen the possibility of a strong interference fit.

The second disadvantage of the Osteonics design is that it has a generally smooth outer surface that does not penetrate bone to enhance fixation. The '549 patent describes an affixation-assisting surface treatment, which should provide some frictional resistance to motion at the fixation interface. However, in practice, this surface treatment has been either a porous metal coating or a knurled surface, neither of which provides fixation ability.

SUMMARY OF THE PRESENT INVENTION

The present invention provides an improved, modified spherical acetabular cup prosthesis. The outer surface of the cup body is spherical in shape with a first radius. Annular grooves or rings are placed adjacent to one another starting at the lower rim of the cup. The bases of the rings follow a second spherical radius such that the first radius is greater than the second radius; and the first radius minus the second radius equals about 0.5 to 2 mm. The first radius and the second radius are tangent to one another at the apex of the cup.

The geometry of the cup of the present invention may also include a series of one or more rings on the surface of the cup which emanate from the apex of the cup body portion in a radial direction to the rim. These grooves interrupt the annular rings at intervals. The purpose of the radial grooves is to reduce the area of each annular ring which must be pushed through bone during impaction. This will decrease the pressure applied to the surrounding bone during insertion, thus facilitate placement of the cup.

The radial grooves may also be advantageous in that, the cup may be turned slightly after impaction into bone. In that case, the radial grooves serve as cutting flutes for the edges of the annular grooves. Turning the cup will cause the edges of the annular rings to cut into bone, providing enhanced fixation.

The geometry described is particularly advantageous for interference fixation of the cup in bone. Because of the relative positions and values of the two spherical radii, the depth of the annular grooves is maximal at the rim of the cup and decreases toward the apex. This facilitates a maximal interference fit at the periphery of the acetabulum, where the quality of bone is usually the best. The shape of the annular rings is designed to provide maximal pullout strength.

For an interference fit, the acetabulum is prepared with a reamer of the second radius. The cup is then impacted into bone, forcing the tips at the sides of each ring to penetrate bone.

In the event that the surgeon prefers a non-interference fit, the cup may be provided with one or more integral holes so that screws or spikes may be used. In that case, the surgeon reams the acetabulum with a reamer of the first radius, positions the cup and places one or more screws or spikes.

Thus, the present invention provides an improved prosthetic joint acetabular cup component that can be press fit into a patient's acetabulum. The acetabular cup component of the present invention includes a shell or body portion having outer convex and inner concave surfaces with an apex portion.

A lower rim portion of the cup body or shell defines a plane. A plurality of annular rings is spaced along the body outer surface between the lower rim and the apex. Each of the rings is preferably parallel to the plane of the lower rim.

The annular rings each comprise upper and lower intersecting annular surfaces. In the preferred embodiment, each ring upper annular surface is inclined with respect to the plane of the lower rim and the rings define a plurality of alternating crests and troughs so that a portion of the surrounding bone tissue can at least partially occupy a trough upon insertion of the body or shell into an acetabulum cavity.

Each ring is spaced a greater distance from the annular rim than the adjacent ring nearest the lower rim. The outer surface portion of the shell is generally hemispherically shaped and there are at least four annular rings on the outer surface of the hemispherically shaped shell, which begin at a position adjacent the lower rim of the shell. The lower annular surface of each ring is substantially parallel to the plane of the lower rim.

The lower annular surface forms an angle with the plane of the lower rim of between 0 and 45 degrees. The upper annular surface forms an angle of 20–60 degrees (preferably 45 degrees) with the plane of the lower rim.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein:

FIG. 3 is a sectional view of the preferred embodiment of the apparatus of the present invention;

FIG. 4–4A are fragmentary views of the preferred embodiment of the apparatus of the present invention illustrating the spacing of annular rings;

FIG. 5 is another fragmentary view of the preferred embodiment of the apparatus of the present invention.

DETAILED DESCRIPTION OF THE PREFERRED EMBODIMENT

Figure 1:
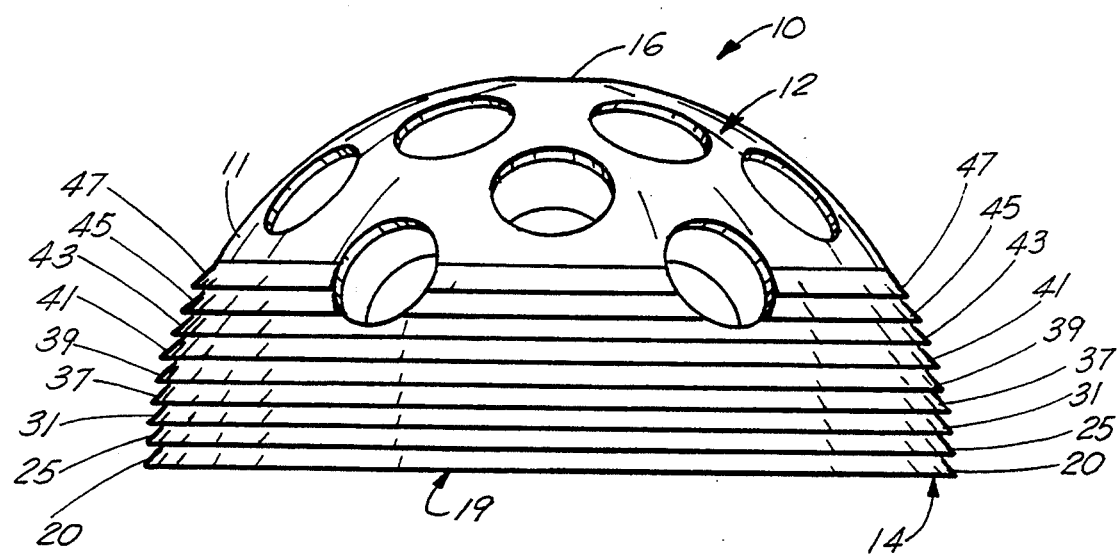
FIG. 1 is a side elevational view of the preferred embodiment of the apparatus of the present invention.
Figure 2:
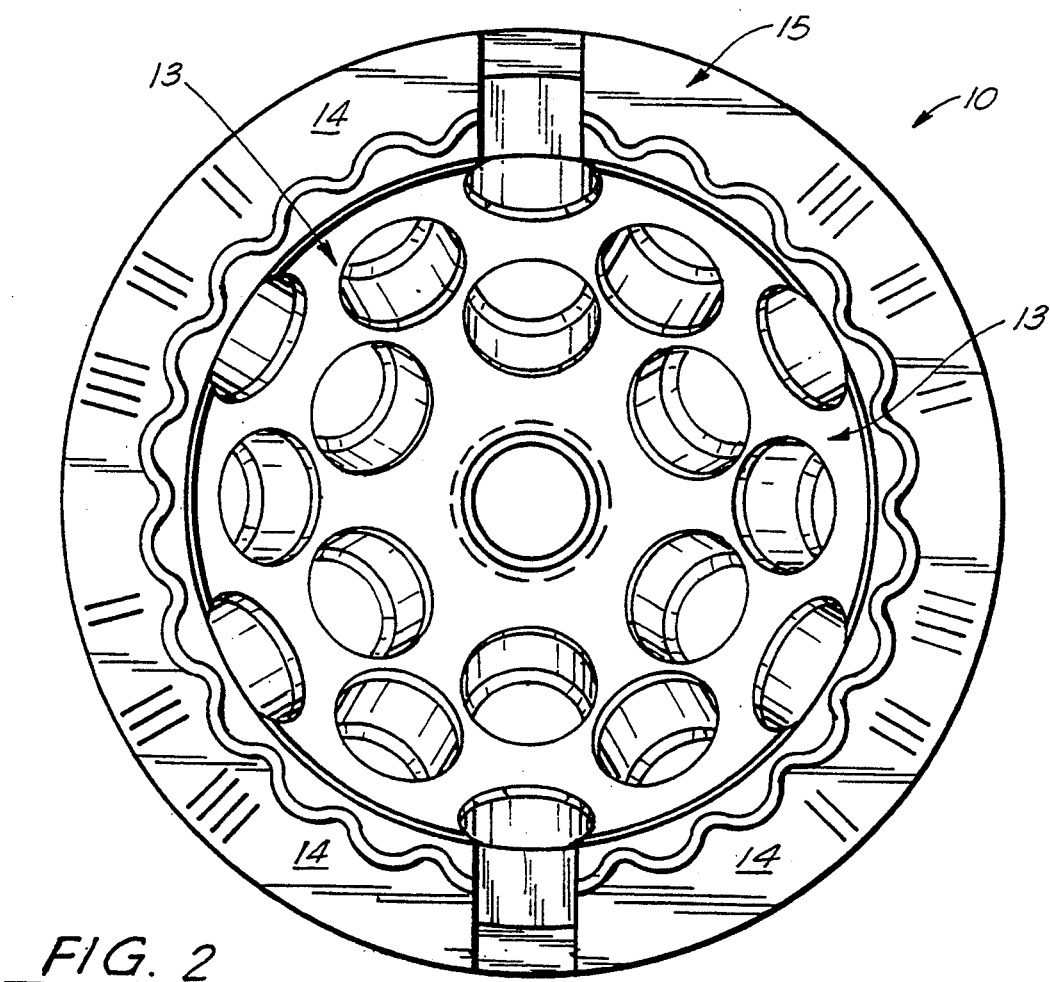
FIG. 2 is a bottom view of the preferred embodiment of the apparatus of the present invention.

FIGS. 1–5 show the preferred embodiment of the apparatus of the present invention designated generally by the numeral 10. Acetabular cup component 10 includes a shell or cup body portion 11 having a convex outer surface 12 and a convex inner surface 13. The cup or shell body 11 provides a lower rim 14 that has a flat annular surface 15 that defines a flat plane 19. The shell or cup body 11 has an apex 16. A first radius 17 tracks the outermost surface of the cup 10. A second and smaller radius 18 tracks and defines the base of the annular rings (see FIG. 3). The plane 19 is the plane defined by the flat annular surface 15.

A plurality of annular rings are spaced apart beginning with and generally parallel to the plane 19 as shown in FIGS. 1–5. The first annular ring 20 includes a lower ring surface 21 and an upper ring surface 22. A projection or crest 23 is defined by the pair of intersecting surfaces 21, 22. A trough 24 separates the first annular ring 20 from a second annular ring 25. The second annular ring 25 also includes a lower annular surface 26 and an upper annular surface 27. A crest 28 is formed by the intersection of the lower surface 26 and the upper surface 27. A trough 29 separates the second annular ring 25 from a third annular ring 31. The arrow 30 defines a dimension line between first and second annular rings 20, 25 (i.e. ring spacing in a direction away from plane 19).

The third annular ring 31 includes a lower ring surface 32 and an upper ring surface 33. The intersection of the upper and lower rings 33, 32 define a crest 34. Trough 35 separates the third 31 and fourth 37 annular rings. Ring spacing arrow 36 (FIGS. 3–4) defines the dimension between second and third rings 25, 31.

Figure 4A:
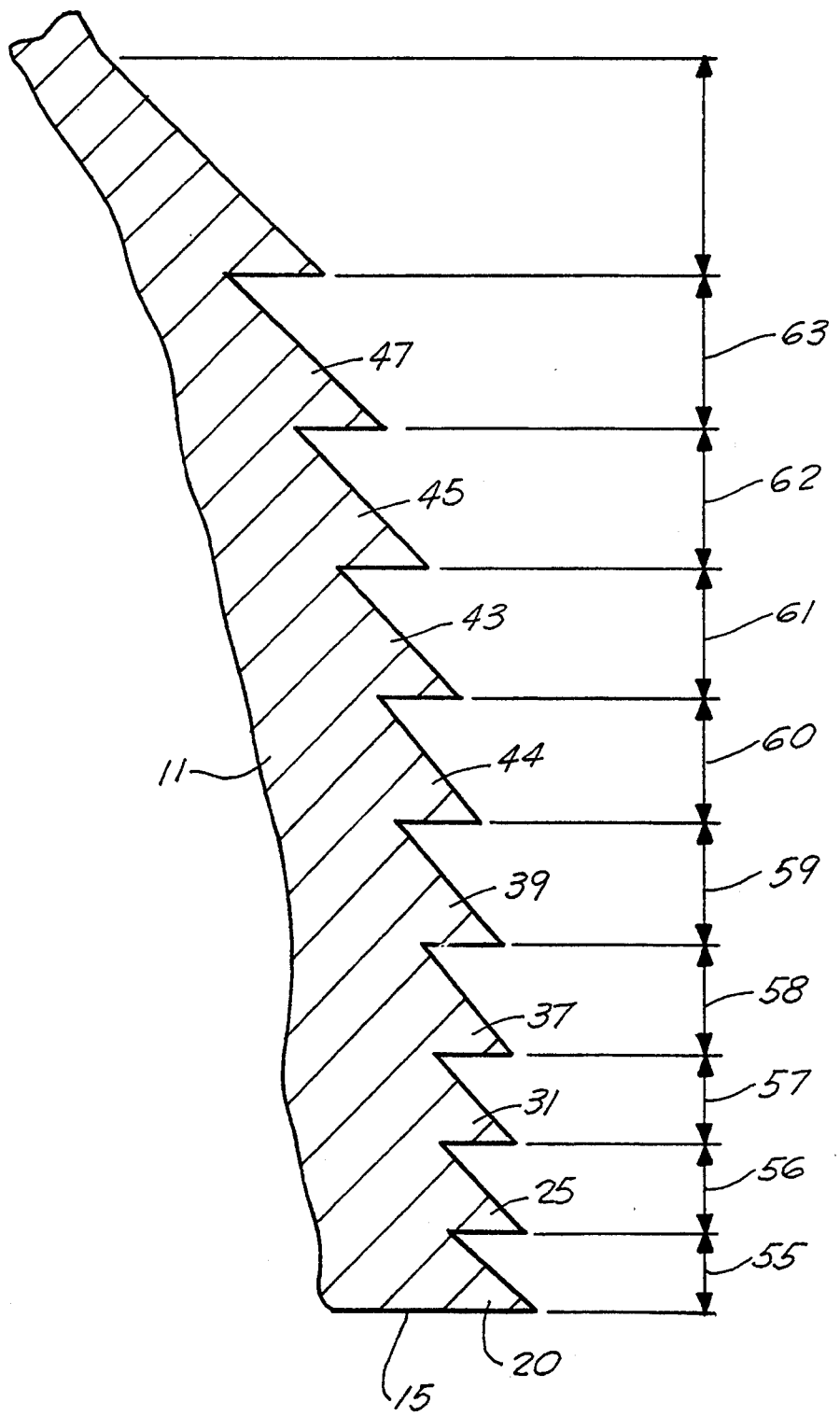

In the drawings, there can be seen forth, fifth, sixth, seventh, eighth, and ninth annular rings designated respectively by the numerals 37, 39, 41, 43, 45 and 47. Spacing between these rings is designated with the rings spacing arrows shown in FIG. 3 including third, fourth, fifth, sixth, seventh, and eighth ring spacing arrows designated respectively by the numerals 38, 40, 42, 44, 46, and 48. In FIGS. 3–4, the spacing between annular rings is constant so that the spacing arrows 38, 40, 42, 44, 46, and 48 are all of the same dimension. In FIG. 4A, annular ring spacing is variable, beginning with a smallest spacing between annular rings 20 and 25 as designated by the dimension arrow 55 designating ring spacing. The spacing between annular rings 25 and 31 is designated by ring spacing arrow 56 which is of a greater dimension than the arrow 55. Each successive dimension between annular rings is greater moving away from flat annular surface 15, so that the dimension arrows 57, 58, 59, 60, 61, 62, 63 are each of increasingly greater dimension, arrow 63 being largest spacing.

The numeral 49 defines an angle of inclination that is preferably a constant angular value for the angle formed by each ring upper surface and plane 19 for all of the ring upper surfaces, such as 22, 27, 33 for example. The preferred value for angle 49 is 45 degrees. The curved line 50 defines the surface as generated by the first radius 17 while the curved line 51 defines the outer surface as defined by the second radius. Arrow 52 designates radius origin spacing between the radius 17 and the radius 18.

Figure 6:
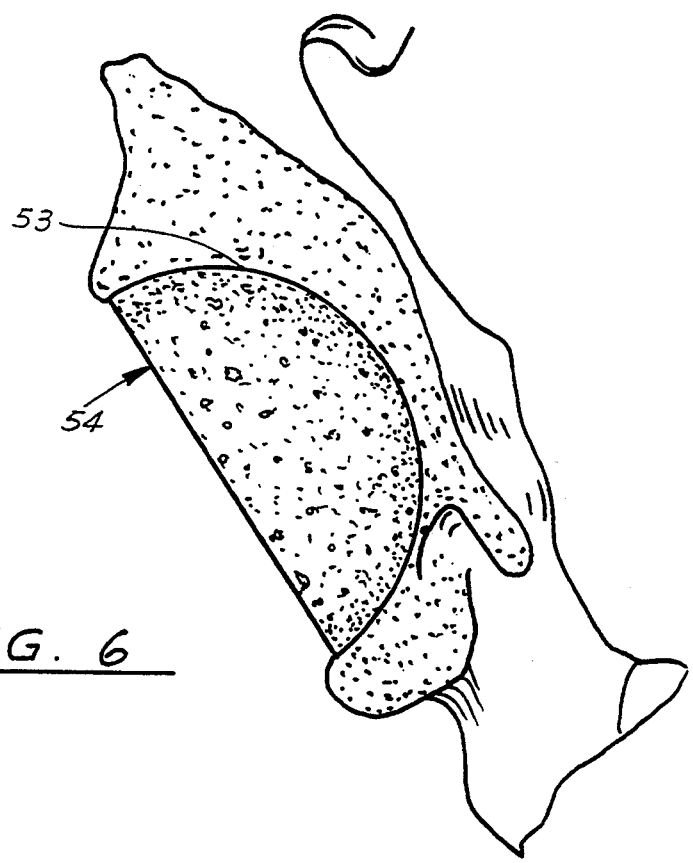
FIGS. 6 and 7 are schematic, sectional views illustrating the patient's acetabulum prior to (FIG. 6) and after (FIG. 7) placement of the acetabular cup of the present invention into operative position.
Figure 7:
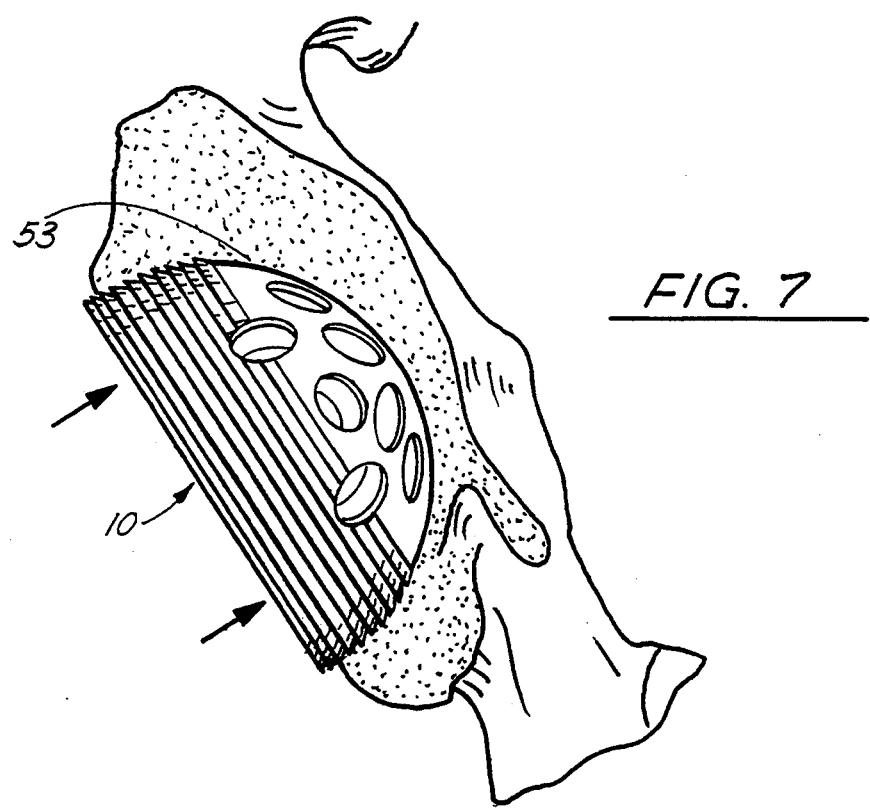

In FIG. 6, a hemispherical socket 54 has been cut in the patents acetabulum. For an interference fit, the socket 54 is cut with a reamer of the second radius 51 and the cup 10 is pressed into socket 54 as shown by the arrows in FIG. 6. For a non-interference fit, the surgeon prepares the socket 54 with a reamer of the first radius 50, and positions the cup 10 using one or more screws or spikes inserted through the openings 56.

The following table lists the part numbers and part descriptions as used herein and in the drawings attached hereto.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A prosthetic joint acetabular cup component, comprising:
   a) a cup body portion having outer convex and inner concave surfaces, an apex portion, and a lower rim portion defining a plane;
   b) a plurality of annular and generally parallel circular rings spaced along the body outer surface between the lower rim and the apex of the cup body, each ring having a crest portion and a trough portion;
   c) the rings each define a plane and, the planes include a plurality of planes that are parallel and of different spacing therebetween, wherein said spacing between at least one adjacent pair of said rings increases in a direction from the lower rim towards said apex portion; and
   d) wherein the outer surface portion has a dual radius curvature.

2. The apparatus of claim 1 wherein the annular rings each comprise upper and lower intersecting annular surfaces.

3. The acetabular cup prosthesis of claim 2 wherein the each ring upper annular surface is inclined with respect to the plane of the lower rim.

4. The acetabular cup prosthesis of claim 1 wherein the rings define a plurality of alternating crests and troughs so that a portion of the surrounding bone tissue can at least partially occupy a trough upon insertion of the body into an acetabulum cavity.

5. A prosthetic joint acetabular cup component, comprising:
   a) a cup body portion having outer convex and inner concave surfaces, an apex portion, and a lower rim portion defining a plane;
   b) a plurality of annular rings spaced along the body outer surface between the lower rim and the apex each ring having an inner base portion; and
   c) wherein the spacing between adjacent pairs of said rings increases in a direction from the lower rim towards said apex portion.

6. The acetabular cup prosthesis of claim 7 wherein the outer surface portion is generally hemispherically shaped.

7. A prosthetic joint acetabular cup component, comprising:
   a) a cup body portion having outer convex and inner concave surfaces, an apex portion, and a lower rim portion defining a plane;
   b) a plurality of annular and generally parallel circular rings spaced along the body outer surface between the lower rim and the apex of the cup body, each ring having a crest portion and a trough portion;
   c) the rings each define a plane and, the planes include a plurality of planes that are parallel and of different spacing therebetween, wherein said spacing between at least one adjacent pair of said rings increases in a direction from the lower rim towards said apex portion; and
   d) wherein the outer surface of the cup body portion is of a first radius, and the crest portion of each of the annular rings follows a curvature defined by a second radius.

8. The acetabular cup prosthesis of claim 7 wherein the first radius is greater than the second radius.

9. The acetabular cup prosthesis of claim 8 wherein the cup body portion has an apex, and the first and second radii are tangent at the apex.

10. The apparatus of claim 2 wherein the lower annular surface of each ring is substantially parallel to the plane of the lower rim.

11. The acetabular cup prosthesis of claim 2 wherein the lower annular surface forms an angle with the plane of the lower rim of between 0 and 45 degrees.

12. The acetabular cup prosthesis of claim 2 wherein the upper annular surface forms an angle of between 20 and 60 degrees with the plane of the lower rim.

* * * * *